(12) United States Patent
Liu et al.

(10) Patent No.: US 11,447,436 B2
(45) Date of Patent: Sep. 20, 2022

(54) METHOD AND SYSTEM TO CONTROL AND MAINTAIN PRODUCT QUALITY FOR AN OLEFIN MEMBRANE SEPARATION

(71) Applicant: UOP LLC, Des Plaines, IL (US)

(72) Inventors: Chunqing Liu, Arlington Heights, IL (US); Trung Pham, Mount Prospect, IL (US); Charles P Luebke, Mount Prospect, IL (US); Carl Liskey, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 17/339,501

(22) Filed: Jun. 4, 2021

(65) Prior Publication Data

US 2021/0403397 A1    Dec. 30, 2021

Related U.S. Application Data

(60) Provisional application No. 63/046,549, filed on Jun. 30, 2020.

(51) Int. Cl.
*C07C 7/144* (2006.01)
*B01D 69/10* (2006.01)
*B01D 53/22* (2006.01)

(52) U.S. Cl.
CPC ........... *C07C 7/144* (2013.01); *B01D 53/228* (2013.01); *B01D 69/10* (2013.01); *B01D 2256/24* (2013.01); *B01D 2257/70* (2013.01); *B01D 2311/06* (2013.01); *B01D 2311/106* (2013.01); *B01D 2311/14* (2013.01); *B01D 2311/26* (2013.01); *B01D 2313/54* (2013.01)

(58) Field of Classification Search
None
See application file for complete search history.

(56) References Cited

U.S. PATENT DOCUMENTS

| | | | |
|---|---|---|---|
| 9,216,931 B1* | 12/2015 | Su | C01B 3/501 |
| 9,346,011 B2* | 5/2016 | Koros | B01D 67/0088 |
| 10,507,435 B1* | 12/2019 | Frey | B01D 71/76 |
| 2004/0173529 A1* | 9/2004 | Da Costa | B01D 61/362 |
| | | | 210/640 |
| 2016/0075619 A1* | 3/2016 | Su | C07C 7/09 |
| | | | 585/809 |
| 2016/0075620 A1* | 3/2016 | Su | C07C 7/005 |
| | | | 585/809 |
| 2017/0050900 A1* | 2/2017 | Su | B01D 53/229 |
| 2017/0354918 A1* | 12/2017 | Liu | B01D 69/10 |
| 2018/0001277 A1* | 1/2018 | Liu | B01D 69/08 |
| 2018/0133644 A1* | 5/2018 | Liu | C10L 3/104 |
| 2018/0345230 A1* | 12/2018 | Karns | B01D 67/0088 |
| 2019/0100479 A1* | 4/2019 | Liu | C07C 7/144 |
| 2019/0193021 A1* | 6/2019 | Rekoske | B01D 53/227 |
| 2020/0101416 A1* | 4/2020 | Liu | B01D 69/142 |
| 2020/0377430 A1* | 12/2020 | Singh | C07C 7/144 |
| 2021/0129085 A1* | 5/2021 | Xu | B01D 67/0067 |

* cited by examiner

*Primary Examiner* — Tam M Nguyen
(74) *Attorney, Agent, or Firm* — Paschall & Associates, LLC; Mark Goldberg

(57) ABSTRACT

A process and system to control the final product quality in a system for separating olefins and paraffins in a membrane system. A small finishing membrane stage is added to an existing membrane system that takes a slip stream from the product, purifies it to a very high concentration of propylene and blends it back into the product stream.

15 Claims, 2 Drawing Sheets

METHOD AND SYSTEM TO CONTROL AND MAINTAIN PRODUCT QUALITY FOR AN OLEFIN MEMBRANE SEPARATION

This application claims priority from provisional patent application 63/046,549 filed Jun. 30, 2020.

BACKGROUND

Membrane technology has been studied in the past to produce polymer grade propylene. For example, there are inventions that relate to installing a membrane module at the overhead of the C3 splitter. Other innovations also investigated integrating membranes around the C3 splitter. However, the one column that cannot be eliminated with any combination of membranes is the C3/C4 splitter because the membrane cannot perform carbon number separation. Therefore, it is advantageous to leverage the C3/C4 splitter as much as possible to minimize the membrane section and overall cost. It is feasible to use a C3/C4 splitter in combination with membranes to produce polymer grade propylene.

In some embodiments of a system containing a C3/C4 splitter and a membrane module, in a revamp application of a C3 splitter adding an olefin/paraffin separation membrane module to increase the capacity to produce polymer grade propylene, it is possible that the system may fall short of delivering a product to the product specification (<99.5% propylene (C3=)). What would be controlling/manipulating variable to bring the product up meet product specification? One of the methods is to increase the purity of the overhead stream from the column or increase purity of the feed going to the membrane. This control method is feasible but may be slow to respond due to the need to increase reflux ratio and other parameters (increased reboiler duty, overhead compression duty, etc.) and may involve further complicated operation. A second method is to vary the permeate pressure (decrease P on the permeate), however, there is not much room or this may be limited by the permeate compressor unit.

DEFINITIONS

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

DETAILED DESCRIPTION

Figure 1:
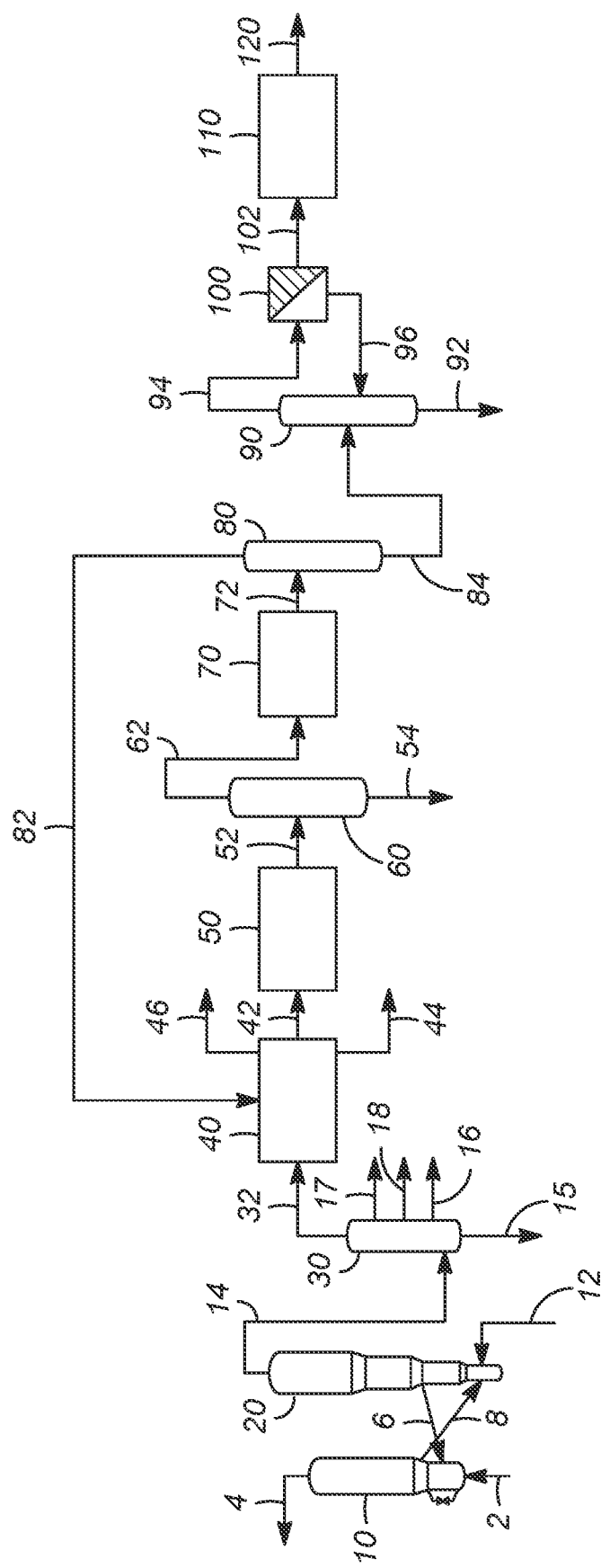
FIG. 1 is a flow scheme for a membrane system for producing light olefins from a hydrocarbon stream.

The following detailed description is merely exemplary in nature and is not intended to limit the application and uses of the embodiment described. Furthermore, there is no intention to be bound by any theory presented in the preceding background or the following detailed description.

The description of the apparatus of this invention is presented with reference to the attached FIGURES. The FIGURES are simplified diagrams of the preferred embodiments of this invention and are not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

As shown in the FIGURES, when the process is working properly a feed stream is sent from a column to a membrane with a composition of about 72 to 85 mol % propylene is contacted with a membrane unit. A permeate stream with a composition of 95 to 99.5 mol % is then compressed up to about 240 psig (1756 kPa). The stream leaving the compression system is then split into two streams. One stream is routed to a cooler exchanger to control at about 40-80° C. (104-176° F.) with a controlled humidity level between 50-99% and is contacted to a finishing membrane unit. The permeate from the finishing unit has a high concentration of propylene, of about 99.5-99.99 mol %, that is recompressed to 240 psig to join with a second portion (from the split upstream of the main membrane unit) to a produce combined product stream that is about 99.5-99.9 mol % propylene. The combined stream is cooled by a cooler/exchanger to 100° F. before going to a receiver to remove free water, followed by regenerable driers before going to product storage. The split stream capacity is within 10-80% flow, or preferably 20-60% flow of the original stream. This split is adjustable and controlled so that the averaged blend composition meets the final product specs of 99.5% C3= or higher (i.e. 99.6%). The proprietary controller (measuring flow and composition) on the main product stream (before split to the finishing membrane), is cascaded to the valve system on the split stream so that the appropriate split flow is allowed/calculated to enter the finishing membrane and the final product composition meets or exceeds 99.5% C3=.

The retentate stream from the finishing membrane unit, with a composition of 90-97 mol % C3=, is mixed with the feed to the main membrane unit to a combined stream with an enriched composition, 74-97 mol % C3=(at least 2 mol % higher than the original feed). The retentate from the main membrane unit has a composition of 40-65 mol % C3= is returning to the column/C3 splitter as a separate or combined feed with the feed to the column.

The finishing membrane unit may produce a permeate stream with pressure higher than 5 psig (136 kPa), or >15 psig (205 kPa), or >35 psig (343 kPa), or >55 psig (481 kPa). The finishing membrane can produce a permeate stream with higher pressure than the main membrane unit. The finishing membrane permeate can be compressed to 240 psig (1756 kPa) with a dedicated compressor or can be compressed in the second stage compression of the main membrane compression unit. By sharing the same compression system, there is a certain advantage in CAPEX, equipment count and may overcome plot space constraint. If sharing compression unit, the finishing membrane unit only includes cooler/heat exchanger, water injection to maintain humidity level, and membrane elements. The finishing membrane unit can be constructed/laid out and integrated with the main membrane module skid/housing and thus may provide additional savings or meet plot space constraint.

The finishing membrane system and method not only applies to a main membrane unit for a hybrid column/splitter+ membrane system but where multiple trains or multiple membrane stages are connected.

A facilitated transport membrane may be used that comprises a nanoporous support membrane, a hydrophilic polymer inside the nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the nanopores can be used as the membranes in the membrane unit described in the present invention. The nanoporous support membrane used for the preparation of the facilitated transport membrane comprising a nanoporous support membrane, a hydrophilic polymer inside the nanopores on the surface of the support membrane, a thin, nonporous, hydrophilic polymer layer coated on the surface of said support membrane, and metal salts incorporated in the hydrophilic polymer layer coated on the surface of the support membrane and said hydrophilic polymer inside the nanopores used in the present invention comprises a polymer selected from a group consisting of, but is not limited to, polyethersulfone (PES), a blend of PES and polyimide, cellulose acetate, cellulose triacetate, and a blend of cellulose acetate and cellulose triacetate. The nanoporous support membrane used in the current invention has an average pore diameter of less than 10 nm on the membrane skin layer surface. The nanoporous support membrane used in the current invention can be either asymmetric integrally skinned membrane or thin film composite (TFC) membrane with either flat sheet (spiral wound) or hollow fiber geometry. The hydrophilic polymer inside the nanopores on the surface of the nanoporous support membrane of the facilitated transport membrane can be selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. The metal salts incorporated in the hydrophilic polymer layer coated on the surface of said support membrane and the hydrophilic polymer inside the nanopores of the facilitated transport membrane are preferred to be selected from silver salts or copper salts, such as silver(I) nitrate or copper(I) chloride. In an embodiment, the dried nanoporous support membrane comprising hydrophilic polymers inside the nanopores on the membrane surface have carbon dioxide permeance of 800-10,000 GPU and no carbon dioxide/methane selectivity at 50° C. under 30-100 psig (308-791 kPa) 10% $CO_2$/90% $CH_4$ mixed gas feed pressure.

The facilitated transport membrane may comprise a nanoporous polyethersulfone/polyvinylpyrrolidone blend support membrane, a hydrophilic polymer inside nanopores of said support membrane, a hydrophilic polymer coating layer on a surface of the support membrane and metal salts in said hydrophilic polymer coating layer and in said hydrophilic polymer inside said nanopores of said support membrane can also be used as the membranes in the membrane unit described in the present invention.

In addition, the membrane may comprise a polyethersulfone/polyethylene oxide-polysilsesquioxane blend support membrane comprising a polyethylene oxide-polysilsesquioxane polymer and a polyethersulfone polymer; a hydrophilic polymer inside the pores on the skin layer surface of the polyethersulfone/polyethylene oxide-polysilsesquioxane blend support membrane; a hydrophilic polymer coated on the skin layer surface of the polyethersulfone/polyethylene oxide-polysilsesquioxane blend support membrane, and metal salts incorporated in the hydrophilic polymer coating layer and the skin layer surface pores of the polyethersulfone/polyethylene oxide-polysilsesquioxane blend support membrane can also be used as the membranes in the membrane unit described in the present invention.

FIG. 1 shows an example of a flowscheme that incorporates the membrane system of the present disclosure into a standard process for producing light olefins from a hydrocarbon feed. In this flowscheme is shown a reactor 20 that takes a hydrocarbon feed 12 that is reacted under standard operating conditions to produce a mixed hydrocarbon reaction product stream 14 which then enters column 30 to be separated into a series of liquid products including a heavy cycle oil product 16, a naphtha product 17 that can be further separated in a naphtha splitter and a light cycle oil product 18. A main column bottoms product stream 15 also known as slurry oil is shown exiting and a vapor stream 32 is then sent to a gas concentration unit 40 from which are shown fuel gas stream 46 exiting to be sent for further treatment, debutanized gasoline stream 44 sent for treatment and a stream 42 that is sent to a sulfur treatment unit 50 in which mercaptans are removed and converted into liquid hydrocarbon disulfides. A resulting light hydrocarbon stream 52 is sent to a C3/C4 splitter 60 with C4s exiting a bottom and other light hydrocarbons in stream 62 being sent for further treatment shown at 70 including contaminant treaters and a hydrogenation unit that removes methyl acetylene and propadiene. Then a hydrocarbon stream 72 is sent to deethanizer 80 with an offgas stream 82 sent back to gas concentration unit 40. Stream 84 is sent to C3 splitter 90 with propane stream 92 sent for separate use and light hydrocarbon stream 94 sent to an olefin/paraffin membrane unit 100 that is shown in greater detail in FIG. 2. A propylene stream 102 is shown passing through compressors/dryers in unit 110 and then compressed dried propylene 120 is sent to storage or further use. A retentate stream 96 is returned to C3 splitter 90.

Figure 2:
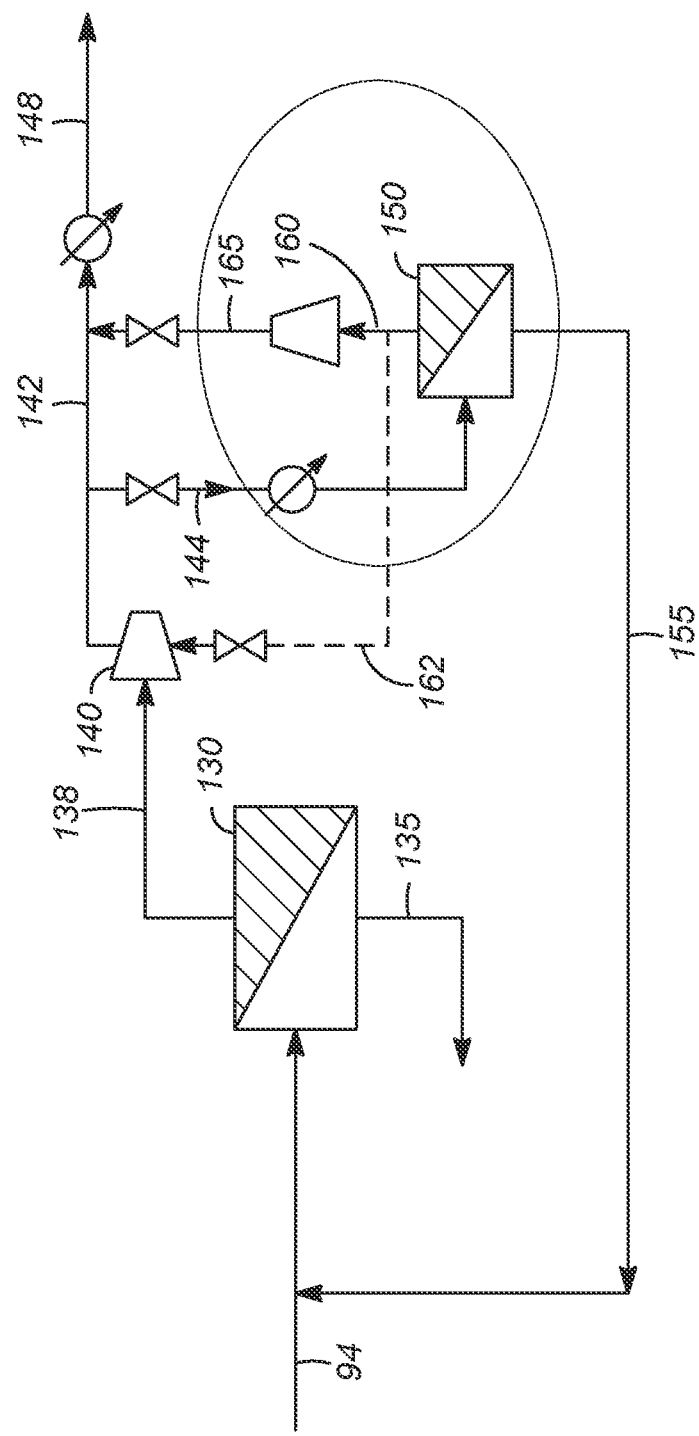
FIG. 2 is a more detailed flow scheme of a membrane system.

In FIG. 2 is shown a more detailed membrane system than the olefin/paraffin membrane unit of FIG. 1. While there may be different concentrations of propylene in the feedstreams, in an example stream 94 comprises about 72-85% propylene and is sent to a set of membrane units 130 that in one configuration include 100 membrane elements. A permeate stream 138 as shown is highly concentrated propylene with 95-99.5 mol % propylene and retentate stream 135 has 40-65 mol % propylene and is returned to the C3 splitter 90 shown in FIG. 1. An additional set of membranes 150 are provided as finishing membranes with 15-35 elements and the capability of handling about 20-60% of the product flow. The finishing stage of membranes is provided for situations when the propylene purity of stream 94 is lower than normal. Stream 142 is a product stream of which a portion 144 may be cooled to about 104-140° F. and then go to finishing membranes 150 with a retentate stream 155 of 90-96% propylene purity returned to stream 94 for further treatment. The resulting stream 94 will have a higher content of propylene due to the relative high level in propylene in retentate stream 155. Also shown are purified propylene stream 160 passing through a compressor to stream 165 to be combined with product stream 148 that is cooled to about 100° F. Valves are shown on lines 144, 165 and 162 so that finishing membranes 150 may be utilized or bypassed depending upon whether or not the propylene in stream 94 is sufficiently concentrated to allow for a 99.5+% propylene product stream to be produced.

SPECIFIC EMBODIMENTS

While the following is described in conjunction with specific embodiments, it will be understood that this description is intended to illustrate and not limit the scope of the preceding description and the appended claims.

A first embodiment of the invention is a process for producing an olefin stream comprising sending a stream comprising about 72-85 mol % olefins to a main membrane unit to produce a first permeate stream comprising about 95-99.5 mol % olefins and a first retentate stream comprising about 40-65 mol % olefins, sending a portion of the first permeate stream to a finishing membrane unit to produce a second permeate stream comprising about 99.5 to 99.99 mol % olefins and a second retentate stream comprising about 90-96 mol % olefins; and combining the second permeate stream with a portion of the first permeate stream to produce a product stream comprising about 99.5-99.9 mol % olefins. An embodiment of the invention is one, any or all of prior embodiments in this paragraph up through the first embodiment in this paragraph wherein the finishing membrane unit has a capacity to process about 15 to 35% of the gas that the main membrane unit has the capacity to process. An embodiment of the invention is one, any or all of prior embodiments in this paragraph up through the first embodiment in this paragraph wherein the second permeate stream is compressed prior to being combined with the first permeate stream. An embodiment of the invention is one, any or all of prior embodiments in this paragraph up through the first embodiment in this paragraph wherein the portion of the first permeate stream is cooled to about 104-140° F. before entering the finishing membrane unit. An embodiment of the invention is one, any or all of prior embodiments in this paragraph up through the first embodiment in this paragraph wherein the portion of the first permeate stream is controlled in response to a sensor measuring the olefin content of the stream comprising about 95-99.5 mol % olefins. An embodiment of the invention is one, any or all of prior embodiments in this paragraph up through the first embodiment in this paragraph wherein the portion of the first permeate stream is about 20-60 mol % of the first permeate stream. An embodiment of the invention is one, any or all of prior embodiments in this paragraph up through the first embodiment in this paragraph wherein the olefins comprise propylene. An embodiment of the invention is one, any or all of prior embodiments in this paragraph up through the first embodiment in this paragraph further comprising compressing and drying the product stream. An embodiment of the invention is one, any or all of prior embodiments in this paragraph up through the first embodiment in this paragraph wherein the portion of the first permeate stream has a humidity level between 50-90%. An embodiment of the invention is one, any or all of prior embodiments in this paragraph up through the first embodiment in this paragraph wherein a controller measures the olefin content of the first permeate stream to determine the amount of the first permeate stream becomes the portion of the first permeate stream. An embodiment of the invention is one, any or all of prior embodiments in this paragraph up through the first embodiment in this paragraph wherein the second permeate stream has a pressure greater than about 136 kPa. An embodiment of the invention is one, any or all of prior embodiments in this paragraph up through the first embodiment in this paragraph wherein the second permeate stream has a pressure greater than about 343 kPa. An embodiment of the invention is one, any or all of prior embodiments in this paragraph up through the first embodiment in this paragraph wherein the second permeate stream has a pressure greater than about 481 kPa. An embodiment of the invention is one, any or all of prior embodiments in this paragraph up through the first embodiment in this paragraph wherein the second permeate stream is compressed by the same compressor that compresses the first permeate stream. An embodiment of the invention is one, any or all of prior embodiments in this paragraph up through the first embodiment in this paragraph wherein the finishing membrane unit is a modular system.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Fahrenheit and, all parts and percentages are by mol, unless otherwise indicated.

The invention claimed is:

1. A process for producing a propylene stream comprising sending a stream comprising about 72-85 mol % propylene to a main membrane unit to produce a first permeate stream comprising about 95-99.5 mol % propylene and a first retentate stream comprising about 40-65 mol % propylene, sending a portion of said first permeate stream to a finishing membrane unit to produce a second permeate stream comprising about 99.5 to 99.99 mol % propylene and a second retentate stream comprising about 90-96 mol % propylene; and combining said second permeate stream with a portion of said first permeate stream to produce a product stream comprising about 99.5-99.9 mol % propylene.

2. The process of claim 1 wherein said finishing membrane unit has a capacity to process about 15 to 35% of the gas that said main membrane unit has the capacity to process.

3. The process of claim 1 wherein said second permeate stream is compressed prior to being combined with said first permeate stream.

4. The process of claim 1 wherein said portion of said first permeate stream is cooled to about 104-140° F. before entering said finishing membrane unit.

5. The process of claim 1 wherein said portion of said first permeate stream is controlled in response to a sensor measuring the propylene content of said stream comprising about 95-99.5 mol % propylene.

6. The process of claim 1 wherein said finishing membrane unit is bypassed if said permeate stream comprises about 99.5-99.9 mol % propylene.

7. The process of claim 1 wherein said portion of said first permeate stream is about 20-60 mol % of the first permeate stream.

8. The process of claim 1 further comprising compressing and drying said product stream.

9. The process of claim 1 wherein said portion of said first permeate stream has a humidity level between 50-90%.

10. The process of claim 1 wherein a controller measures the propylene content of said first permeate stream to determine the amount of said first permeate stream becomes said portion of said first permeate stream.

11. The process of claim 1 wherein said second permeate stream has a pressure greater than about 136 kPa.

12. The process of claim 1 wherein said second permeate stream has a pressure greater than about 343 kPa.

13. The process of claim 1 wherein said second permeate stream has a pressure greater than about 481 kPa.

14. The process of claim 1 wherein said second permeate stream is compressed by the same compressor that compresses said first permeate stream.

15. The process of claim 1 wherein said finishing membrane unit is a modular system.

\* \* \* \* \*